United States Patent [19]

Landscheidt et al.

[11] Patent Number: 5,648,500
[45] Date of Patent: Jul. 15, 1997

[54] PROCESS FOR THE PREPARATION OF SUBSTITUTED 1,2,3,4-TETRAHYDROCARBAZOLES

[75] Inventors: Heinz Landscheidt, Duisburg; Alexander Klausener; Eberhard Zirngiebl, both of Köln; Jörg-Dietrich Jentsch, Ruhr, all of Germany

[73] Assignee: Bayer Aktiengesellschaft, Leverkusen, Germany

[21] Appl. No.: 608,869

[22] Filed: Feb. 29, 1996

[30] Foreign Application Priority Data

Mar. 6, 1995 [DE] Germany .................. 195 07 751.2

[51] Int. Cl.⁶ .................................................. C07D 209/88
[52] U.S. Cl. .................................... 548/440; 548/441
[58] Field of Search ...................... 548/440, 441

[56] References Cited

U.S. PATENT DOCUMENTS

| | | |
|---|---|---|
| 3,959,309 | 5/1976 | Mooradian . |
| 4,827,032 | 5/1989 | Böshagen et al. . |
| 4,988,820 | 1/1991 | Böshagen et al. . |

FOREIGN PATENT DOCUMENTS

| | | |
|---|---|---|
| 0179217 | 4/1986 | European Pat. Off. . |
| 3631824 | 3/1988 | Germany . |

OTHER PUBLICATIONS

Billman, J.H. et al., *J. Am. Chem. Soc.*, 75, 1345–1346, Mar. 20, 1953.

*Primary Examiner*—Jacqueline Haley
*Attorney, Agent, or Firm*—Sprung Horn Kramer & Woods

[57] ABSTRACT

Substituted 1,2,3,4-tetrahydrocarbazoles of the formula

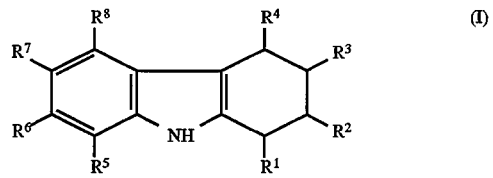

having the meaning for $R^1$ to $R^8$ indicated in the description, can be prepared by catalytically hydrogenating a substituted phenol of the formula

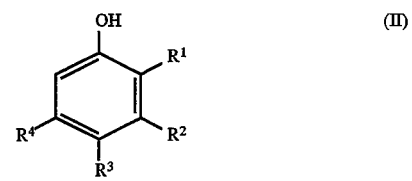

reacting the hydrogenation solution with a phenylhydrazine of the formula

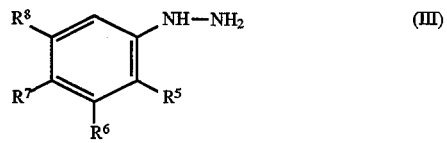

to give the hydrazone and cyclizing the hydrazone under acidic conditions.

15 Claims, No Drawings

PROCESS FOR THE PREPARATION OF SUBSTITUTED 1,2,3,4-TETRAHYDROCARBAZOLES

The present invention relates to a process for the preparation of substituted 1,2,3,4-tetrahydrocarbazoles by heterogeneously catalysed selective nuclear hydrogenation of substituted phenols and subsequent reaction of the substituted cyclohexanones thus obtained with optionally substituted phenylhydrazines.

Substituted 1,2,3,4-tetrahydrocarbazoles are of importance as intermediates for the production of pharmaceutical active compounds. The use of compounds of this type as medicaments is thus described in U.S. Pat. No. 4,988,820 and DE 3,63 1,824.

Substituted 1,2,3,4-tetrahydrocarbazoles can generally be prepared by reaction of substituted cyclohexanones with phenylhydrazine and subsequent cyclization of the intermediately obtained substituted phenylhydrazones in the presence of acid. This process is a special embodiment of the Fischer indole synthesis. U.S. Pat. No. 3,959,309 describes, for example, the reaction of 4-acetamido-cyclohexanone and phenylhydrazine to give 3-acetamido-1,2,3,4-tetrahydrocarbazole.

It is problematic that the substituted cyclohexanones needed, as a rule, are not accessible in a simple manner, but have to be obtained by complicated oxidation processes. In order not to have to accept a reduction in yield in the following reaction steps and in order to avoid possible contaminations of the pharmaceutically active target compounds with the oxidizing agents, in general heavy metal compounds, used for the preparation of the substituted cyclohexanones mentioned, the cyclohexanones thus obtained must be subjected to a complicated purification procedure, whereby the synthesis of the desired substituted 1,2,3,4-tetrahydrocarbazoles is made considerably more expensive.

It was therefore the object, starting from easily accessible and, if possible, already industrially available raw materials, to find a simplified process for the preparation of substituted 1,2,3,4-tetrahydrocarbazoles.

The invention relates to a process for the preparation of substituted 1,2,3,4-tetrahydrocarbazoles of the formula

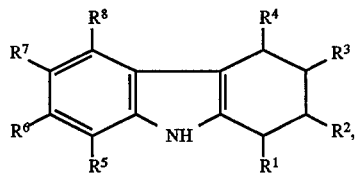

(I)

in which $R^1$, $R^2$, $R^3$ and $R^4$ independently of one another denote hydrogen, $C_1$–$C_4$-alkyl, $C_3$–$C_8$-cycloalkyl, halogen, hydroxyl, $C_1$–$C_4$-alkoxy, $C_3$–$C_8$-cycloalkoxy, $C_1$–$C_4$-alkylamino, $N(C_1$–$C_4$-alkyl)$_2$-, NH—$C_1$–$C_4$-acyl, COOH, —COO$C_1$–$C_4$-alkyl or —CH$_2$—Q, where Q represents hydroxyl, $C_1$–$C_4$-alkoxy or NH—$C_1$–$C_4$-acyl and where at least one of $R^1$ to $R^4$ is other than hydrogen, and in which $R^5$, $R^6$, $R^7$ and $R^8$ independently of one another denote hydrogen, $C_1$–$C_4$-alkyl halogen or $C_1$–$C_4$-alkoxy, which is characterized in that a substituted phenol of the formula

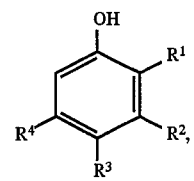

(II)

in which $R^1$, $R^2$, $R^3$ and $R^4$ have the meaning indicated above, is catalytically hydrogenated in the presence of a catalyst from the series of metals of group VIII B of the Periodic Table of the Elements (Mendeleev), which is optionally applied to a support, and, if appropriate, in the presence of one or more further additives from the series of alkaline-reacting alkali(ne earth) metals or ammonium salts in one or more ethers as solvents, the hydrogenation solution obtained after removal of the catalyst is reacted with a phenylhydrazine of the formula

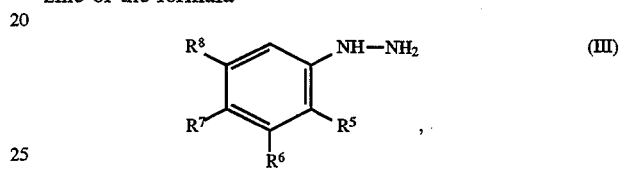

(III)

in which $R^5$, $R^6$, $R^7$ and $R^8$ have the meaning indicated above, if appropriate after addition of water, and the substituted phenylhydrazone obtained in this process as an intermediate is subjected, preferably after intermediate isolation, to an intramolecular cyclization under acidic conditions.

Halogen is, for example, fluorine, chlorine or bromine, preferably chlorine.

$C_1$–$C_4$-alkyl is, for example, methyl, ethyl, propyl, isopropyl, butyl, isobutyl, sec-butyl or tert-butyl, preferably methyl or ethyl, particularly preferably methyl.

$C_1$–$C_4$-alkoxy is, for example, methoxy, ethoxy, propoxy, isopropoxy, butoxy, isobutoxy, sec-butoxy or tert-butoxy, preferably methoxy or ethoxy, particularly preferably methoxy.

$C_3$–$C_8$-cycloalkyl is, for example, cyclopropyl, cyclobutyl, cyclopentyl, cyclohexyl, cycloheptyl, cyclooctyl, mono-, di-, tri- or tetramethyl-substituted cycloalkyl of the type mentioned having a total of up to 8 C atoms or correspondingly ethyl-substituted cycloalkyl, preferably cyclopropyl, cyclopentyl, cyclohexyl or methyl- or ethyl-substituted derivatives thereof.

$C_3$–$C_8$-cycloalkoxy derives from the cycloalkyl mentioned in a manner analogous to alkoxy from alkyl.

$C_1$–$C_4$-acyl is, for example, formyl, acetyl, propionyl, n-butyryl or i-butyryl, preferably acetyl.

Preferably, a phenol of the formula

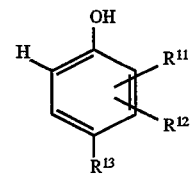

(IV)

is employed in which $R^{11}$ and $R^{12}$ independently of one another denote hydrogen, $C_1$–$C_4$-alkyl, $C_1$–$C_4$-alkoxy, chlorine or hydroxyl and $R^{13}$ represents hydroxyl, $C_1$–$C_4$-alkyl, $C_1$–$C_4$-alkoxy, $C_1$–$C_4$-alkylamino, $N(C_1$–$C_4$-alkyl)$_2$, NH-$C_1$–$C_4$-acyl or —COO—$C_1$–$C_4$-alkyl.

Particularly preferably, a phenol of the formula

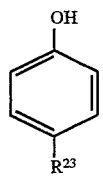

(V)

is employed in which
$R^{23}$ denotes hydroxyl, methoxy, ethoxy, methylamino, dimethylamino or acetamido.

In a furthermore preferred form, a phenylhydrazine of the formula

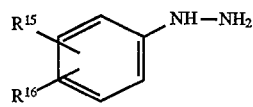

(VI)

is employed in which $R^{15}$ and $R^{16}$ independently of one another denote hydrogen, methyl, methoxy or chlorine.

Particularly preferably, non-substituted phenylhydrazine is employed.

To carry out the process according to the invention, the substituted phenol of the formula (II) is dissolved or suspended in a solvent from the group consisting of the ethers, preferably in diethylene glycol dimethyl ether, ethylene glycol dimethyl ether, dioxane or tetrahydrofuran, in a weight ratio of 2:1 to 1:10 (phenol/solvent), optionally at elevated temperature, and treated with a catalyst from the group consisting of the metals of group VIII B of the Periodic Table of the Elements (Mendeleev), which has optionally been applied to a solid support material, such as active carbon, $Al_2O_3$, $SiO_2$, inter alia, in a weight ratio of 10,000:1 to 10:1 (phenol/catalyst), and optionally with an alkaline-reacting alkali(ne earth) metal or ammonium salt in a weight ratio of 20,000:1 to 20:1 (phenol/additive).

Metals of group VIII B of the Periodic Table are, for example, palladium, ruthenium, rhodium, platinum or nickel, preferably palladium. Preferably, palladium is employed on a support, particularly preferably on active carbon.

Alkaline-reacting salts which can be employed as additives are, for example, the hydroxides, hydrides, carbonates, hydrogen carbonates, sulphites, sulphides, phosphates, hydrogen phosphates, borohydrides, borates and $C_1$–$C_6$-carboxylates of Li, Na, K, Rb, Cs, Mg, Ca, Sr, Ba, $NH_4^+$ or substituted $NH_4^+$, preferably the carbonates, hydrogen carbonates, borates, formates and acetates of Na, K, Ca and Mg, e.g. sodium carbonate and borax.

The heterogeneously catalysed hydrogenation according to the invention is carried out with stirring at a temperature of 20° C. to 250° C., preferably 60° to 230° C., particularly preferably 100° to 210° C., and a hydrogen pressure of 1 bar to 200 bar, preferably 2 to 150 bar, particularly preferably 3 to 100 bar. In the hydrogenation, to achieve the optimum selectivity, the amount of hydrogen absorbed is expediently shown in order to be able to terminate the hydrogenation on reaching the precalculated amounts of hydrogen of 1.5 to 2.5 mol of hydrogen per mole of phenol. This can be achieved by decreasing the stirrer speed, lowering the temperature and/or interrupting the addition of hydrogen.

After completion of the hydrogenation according to the invention, the catalyst is separated off with the aid of customary techniques, for example by filtration.

In the further course of the process according to the invention, the reaction mixture, if appropriate with addition of 50–2000 ml, preferably 100–1000 ml, of water per mole of phenol employed, is treated with 0.5 to 1.5 mol of the optionally substituted phenylhydrazine of the general formula (III) per mole of phenol employed and the substituted phenylhydrazone which is formed in this process and virtually completely precipitated is filtered off after a reaction time of approximately 1 to 48 hours.

By heating the said intermediately formed substituted phenylhydrazone in the presence of acid, preferably in the presence of acid which is optionally diluted with water, the desired substituted 1,2,3,4-tetrahydrocarbazole of the general formula (I) is obtained, which, after cooling the reaction mixture, precipitates and can be isolated in pure form, for example by filtration.

The acids used for carrying out the process according to the invention are mineral acids, such as HCl, $H_2SO_4$ or $H_3PO4$, or alkanecarboxylic acids having 1–6 C atoms, preferably alkanecarboxylic acids having 1 to 3 C atoms, particularly preferably acetic acid. The amount of acid is 0.5–20 mol, preferably 1–10 equivalents, per mole of phenol employed. The dilution water is 1–100 ml per equivalent of acid.

EXAMPLES

Example 1

A mixture of 150 g of hydroquinone and 150 ml of diethylene glycol dimethyl ether was hydrogenated at 160° C. and a pressure of 10 bar in the presence of 3 g of Pd (5% by weight) on active carbon and with addition of 0.5 g of borax. After absorption of 90 l of hydrogen, the hydrogenation was interrupted, the catalyst was filtered off and the solution was treated, after addition of 500 ml of water, with 120 g of phenylhydrazine with stirring. The mixture was subsequently allowed to react at room temperature for 24 h, and the hydrazone was filtered off and washed with water. The hydrazone thus obtained was heated under reflux for 2 h with 300 ml of 40% strength aqueous acetic acid without further purification. After cooling to room temperature, the mixture was allowed to stand at 10° C. for a further 0.5 h and the precipitated product was filtered off with suction. 160 g of 3-hydroxy-1,2,3,4-tetrahydrocarbazole (m.p. 140° C.) were obtained in this way.

Example 2

A mixture of 150 g of 4-methoxy-phenol and 150 ml of diethylene glycol dimethyl ether was hydrogenated at 160° C. and a pressure of 10 bar in the presence of 3 g of Pd (5% by weight) on active carbon and with addition of 0.5 g of borax. After absorption of 90 l of hydrogen, the hydrogenation was interrupted, the catalyst was filtered off and the solution was treated, after addition of 500 g of water, with 110 g of phenylhydrazine with stirring. The mixture was subsequently allowed to react at room temperature for 24 h, and the hydrazone was filtered off and washed with water. The hydrazone thus obtained was heated under reflux for 2 h with 300 ml of 40% strength aqueous acetic acid without further purification. After cooling to room temperature, it was allowed to stand at 10° C. for a further 0.5 h and the precipitated product was filtered off with suction. 160 g of 3-methoxy-1,2,3,4-tetrahydrocarbazole (m.p.: 105° C.) were obtained in this way.

Example 3

A mixture of 150 g of 4-acetamido-phenol and 150 ml of diethylene glycol dimethyl ether was hydrogenated at 160°

C. and a pressure of 10 bar in the presence of 3 g of Pd (5% by weight) on active carbon and with addition of 0.5 g of borax. After absorption of 90 l of hydrogen, the hydrogenation was interrupted, the catalyst was filtered off and the solution was treated, after addition of 500 ml of water, with 120 g of phenylhydrazine with stirring. The mixture was subsequently allowed to react at room temperature for 24 h, and the hydrazone was filtered off and washed with water. The hydrazone thus obtained was heated under reflux for 2 h with 300 ml of 40% strength aqueous acetic acid without further purification. After cooling to room temperature, it was allowed to stand at 10° C. for a further 0.5 h and the precipitated product was filtered off with suction. 150 g of 3-acetamido-1,2,3,4-tetrahydrocarbazole (m.p. 170° C.) were obtained in this way.

What is claimed is:

1. A process for the preparation of a substituted 1,2,3,4-tetrahydrocarbazole of the formula

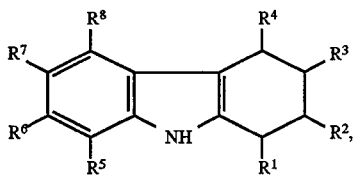

in which $R^1$, $R^2$, $R^3$ and $R^4$ independently of one another are selected from hydrogen, $C_1$–$C_4$-alkyl, $C_3$–$C_8$-cycloalkyl, halogen, hydroxyl, $C_1$–$C_4$-alkoxy, $C_3$–$C_8$-cycloalkoxy, $C_1$–$C_4$-alkylamino, $N(C_1$–$C_4$-alkyl$)_2$-, NH—$C_1$–$C_4$-acyl, COOH, —COO$C_1$–$C_4$-alkyl and —CH$_2$—Q, where Q represents hydroxyl, $C_1$–$C_4$-alkoxy or NH-$C_1$–$C_4$-acyl and where at least one of $R^1$ to $R^4$ is other than hydrogen, and in which $R^5$, $R^6$, $R^7$ and $R^8$ independently of one another are selected from hydrogen, $C_1$–$C_4$-alkyl, halogen or $C_1$–$C_4$-alkoxy, in which a substituted phenol of the formula

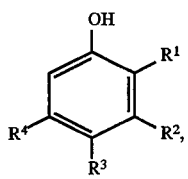

in which $R^1$, $R^2$, $R^3$ and $R^4$ have the meaning indicated above, is catalytically hydrogenated in the presence of a catalyst from the series of metals of group VIII B of the Periodic Table of the Elements (Mendeleev) in one or more ethers as solvents, the hydrogenation solution obtained after removal of the catalyst is reacted with a phenylhydrazine of the formula

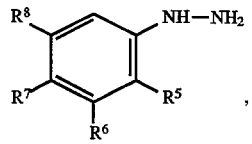

in which $R^5$, $R^6$, $R^7$ and $R^8$ have the meaning indicated above, and the substituted phenylhydrazone obtained in this process as an intermediate is subjected, after optionally isolating the intermediate, to an intramolecular cyclization under acidic conditions.

2. The process of claim 1, in which the catalyst is applied to a support.

3. The process of claim 1, which is carried out in the presence of one or more additives of alkaline-reacting alkali(ne earth) metals or ammonium salts.

4. The process of claim 1, in which the reaction with the phenylhydrazine is carried out after addition of water.

5. The process of claim 1, in which the substituted phenylhydrazone, after intermediate isolation, is subjected to intramolecular cyclization.

6. The process of claim 1, in which the hydrogenation is carried out in diethylene glycol dimethyl ether, ethylene glycol dimethyl ether, 1,4-dioxane, tetrahydrofuran or a mixture of several of these.

7. The process of claim 1, in which the substituted phenol employed is hydroquinone, 4-methoxy-phenol or p-acetylamino-phenol.

8. The process of claim 1, in which the hydrogenation is carried out in a temperature range from 20° C. to 250° C.

9. The process of claim 1, in which the hydrogenation is carried out in a pressure range from 1 bar to 200 bar.

10. The process of claim 1, in which the catalyst employed is palladium on a support.

11. The process of claim 1, in which the catalyst employed is palladium on carbon.

12. The process of claim 1, which is carried out in the presence of an additive which is sodium carbonate or borax.

13. The process of claim 1, in which non-substituted phenylhydrazine is employed.

14. The process of claim 1, in which, for carrying out the cyclization step, the acid employed is an aqueous alkanecarboxylic acid having 1 to 3 C atoms in a mixture with water.

15. The process of claim 1, in which, for carrying out the cyclization step, the acid employed is acetic acid in a mixture with water.

* * * * *